United States Patent [19]

Liddle

[11] Patent Number: Plant 5,488

[45] Date of Patent: Jun. 11, 1985

[54] CUPRESSUS MACROCARPA

[76] Inventor: Donald J. Liddle, 42 Ngarara Rd., Waikanae, Wellington, New Zealand

[21] Appl. No.: 482,620

[22] Filed: Apr. 6, 1983

[51] Int. Cl.[3] ..... A01H 5/00

[52] U.S. Cl. ..... Plt./50

[58] Field of Search ..... Plt./50

*Primary Examiner*—Robert E. Bagwill

*Attorney, Agent, or Firm*—Vincent G. Gioia

[57] ABSTRACT

A new *Cupressus macrocarpa* which is a sport of the *Cupressus macrocarpa* known as "Cupressus Gold Spread".

3 Drawing Figures

1

The present invention relates to a new and distinct variety of *Cupressus macrocarpa* which was discovered by me in Waikanae, New Zealand as a sport of the *Cupressus macrocarpa* "Gold Spread". The denomination of the new variety is "Golden Halo". The following is a detailed description of my new variety, from observations made of specimens grown outdoors at Waikanae, New Zealand. Color terminology is in accordance with The Royal Horticultural Society Colour Chart (R.H.S.).

Among the novel characteristics possessed by this new variety which distinguish it from the cultivar from which it sported and from all other varieties of which I am aware are:

Plants of "Golden Halo" have a low spreading habit; branches arch from the base and become horizontal, producing a low umbrella-shaped shrub of substantial structure. A plant of the new variety can achieve a size of three meters in spread and one meter in height.

The bark of old wood is red-brown; current season's shoots are yellow (R.H.S. 5B in summer, R.H.S. 154B-D in autumn) with the tip of the scales being yellow-green (R.H.S. 144B-D in autumn). Foliage color in spring corresponds to R.H.S. 144C with R.H.S. 143C at the tip of the scale leaves. In summer, foliage color of plants grown in full sunlight corresponds to R.H.S. 5A with R.H.S. 154B at the tips of the scale leaves. The parent variety "Gold Sread" has greener foliage: R.H.S. 137D-143C in spring, R.H.S. 150B in summer.

"Golden Halo" plants have an outward facing branch system with stiff branchlets; terminal branchlets arise at an angle of approximately 45° from the axis. Growth of "Gold Spread" is more dense, branchlets are more flexible and terminal branchlets arise from the axis at an angle of approximately 30°.

Internode length on the main stems of the new variety are (7)-9-(11) mm, scale leaves are 2.5–3.5 mm long

2 and 1.0–2.0 mm wide, with prominent glands and strong citrus fragrance.

No evidence of sexual features were noted on a plant aged seven years.

Asexual reproduction by cuttings of the new variety as performed in Waikanae, New Zealand shows that the foregoing and other distinguishing characteristics come true to form and are established and transmitted through succeeding propagations.

The drawing accompanying the application as filed, FIG. 1, shows a plant of "Golden Halo", age eight years with typical growth habit and foliage characteristics, depicted in color as nearly true as it is reasonably possible to make the same in a color illustration of this character.

Figure 1:
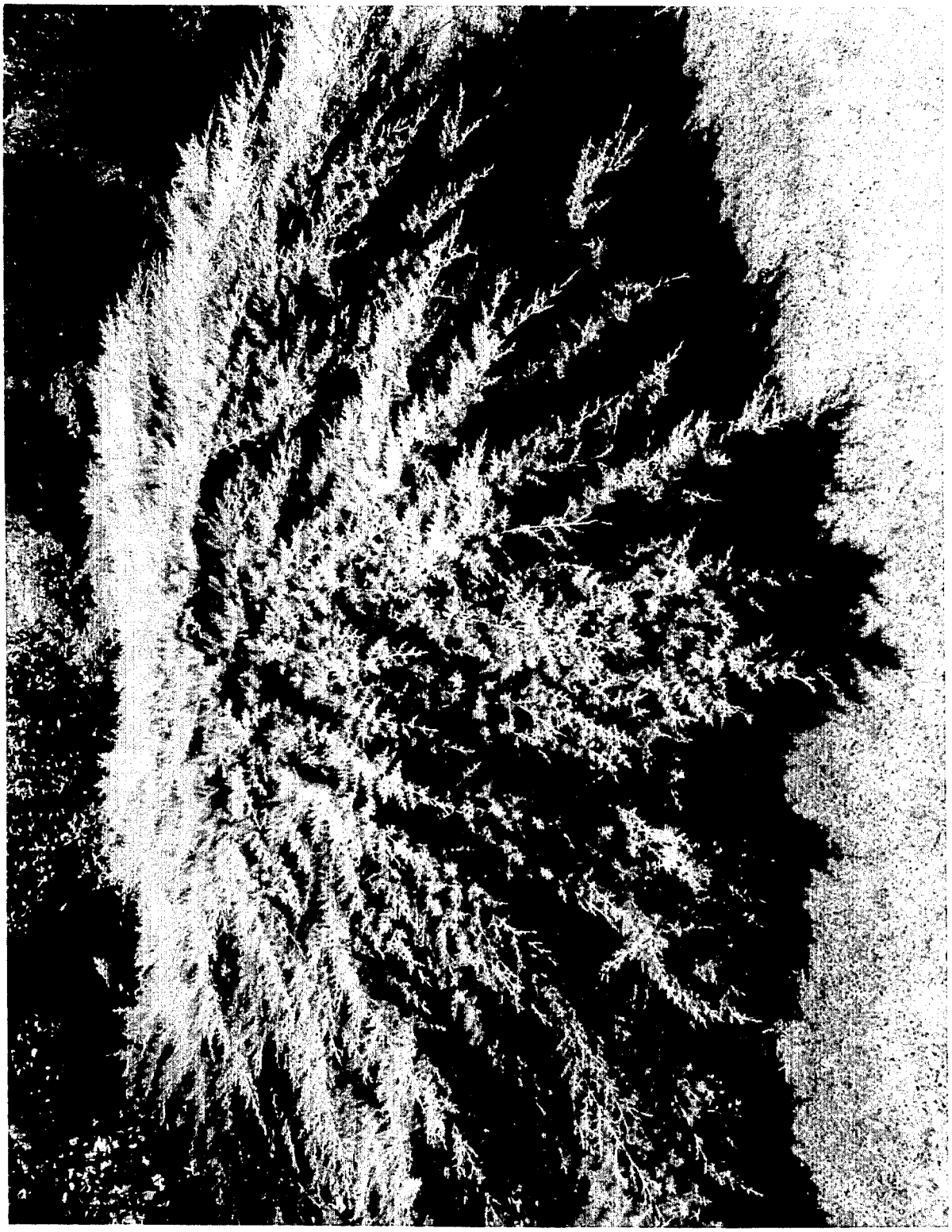
Figure 2:
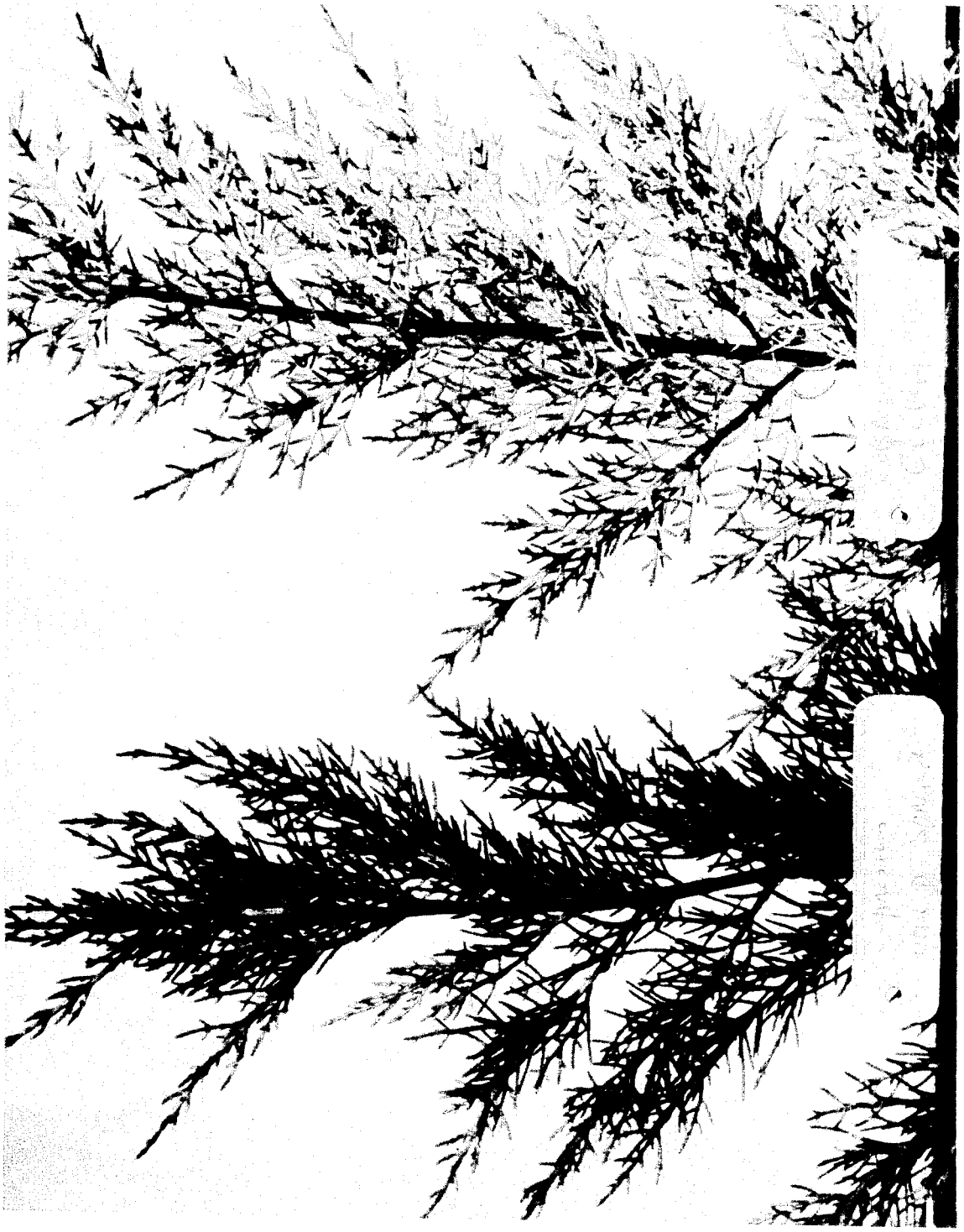
FIG. 2 shows a typical foliage specimen of "Golden Halo" in summer, and a typical foliage specimen of the parent variety "Gold Spread" in summer.
Figure 3:
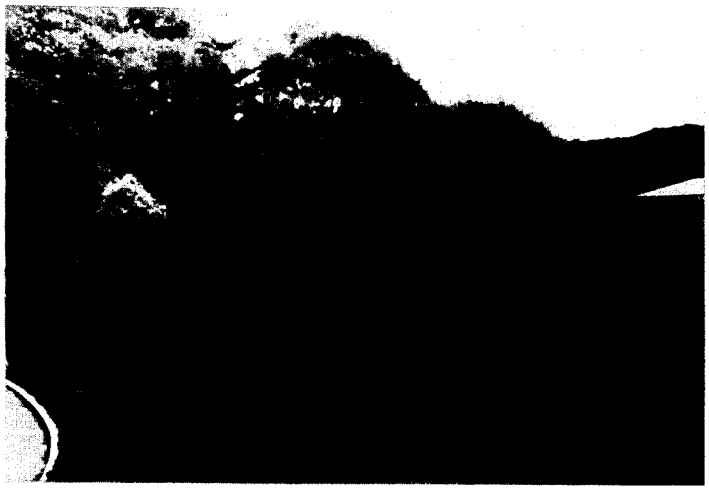
FIG. 3 shows a plant of "Golden Halo" in the foreground with typical cascading effect of branches after light rain.

Mutation: Of *Cupressus macrocarpa* known as "Cupressus Gold Spread ".

Class: The Cypress (*Cupressus macrocarpa*).

An application for Plant Selectors's Rights and Protective Direction for the Cupressus variety "Golden Halo" was accepted by the Plant Varieties Office of New Zealand on Apr. 6, 1982.

I claim:

1. A new and distinct variety of Cypress *Cupressus macrocarpa* named "Golden Halo" substantially as shown and described which is a sport of the *Cupressus macrocarpa* "Gold Spread" characterized particularly by low spreading habit and unique arching of branches from the base, stiff outward facing branching system, and by bright yellow coloring of the foliage, being most pronounced in the new stem growth in summer.

* * * * *